(12) United States Patent
Laurence et al.

(10) Patent No.: US 8,987,659 B2
(45) Date of Patent: Mar. 24, 2015

(54) PET CALIBRATIONS WITH VARYING COINCIDENCE WINDOWS

(75) Inventors: Thomas Leroy Laurence, North Royalton, OH (US); Jeffrey Allan Kolthammer, Cleveland Heights, OH (US)

(73) Assignee: Koninklijke Philips N.V., Eindhoven (NL)

(*) Notice: Subject to any disclaimer, the term of this patent is extended or adjusted under 35 U.S.C. 154(b) by 204 days.

(21) Appl. No.: 13/885,282

(22) PCT Filed: Nov. 15, 2011

(86) PCT No.: PCT/IB2011/055097
§ 371 (c)(1),
(2), (4) Date: May 14, 2013

(87) PCT Pub. No.: WO2012/069960
PCT Pub. Date: May 31, 2012

(65) Prior Publication Data
US 2013/0240721 A1   Sep. 19, 2013

Related U.S. Application Data

(60) Provisional application No. 61/416,323, filed on Nov. 23, 2010.

(51) Int. Cl.
*G12B 13/00* (2006.01)
*G01T 1/164* (2006.01)
*G01T 1/29* (2006.01)
(Continued)

(52) U.S. Cl.
CPC .............. *G01T 1/164* (2013.01); *G01T 1/2964* (2013.01); *G01T 1/1648* (2013.01); *G01T 1/2985* (2013.01); *A61B 6/583* (2013.01); *A61B 6/037* (2013.01)
USPC .................................. 250/252.1; 250/363.03

(58) Field of Classification Search
USPC .......................................... 250/252.1, 363.03
See application file for complete search history.

(56) References Cited

U.S. PATENT DOCUMENTS

| 7,057,178 B1 | 6/2006 | Manjeshwar et al. |
| 7,227,149 B2 | 6/2007 | Stearns et al. |

(Continued)

FOREIGN PATENT DOCUMENTS

JP   11153669 A   6/1999

OTHER PUBLICATIONS

Boellaard et al., Effects of Noise, Image Resolution, and ROI Definition on the Accuracy of Standard Uptake Values: a Simulation Study, Sep. 2004, Journal of Nuclear Medicine, vol. 45, pp. 1519-1527.*

(Continued)

*Primary Examiner* — Christine Sung

(57) ABSTRACT

When calibrating a positron emission tomography (PET) scanner, a radioactive calibration phantom is scanned over a period of several half lives to acquire a plurality of frames of scan data. Interlaced timing windows are employed to facilitate acquiring coincidence data for a plurality of coincidence timing windows and energy windows during a single calibration scan. Coincident events are binned according to each of a plurality of selected coincidence windows, and the PET scanner is calibrated for each of the plurality of coincidence timing windows using data acquired from the single calibration scan.

22 Claims, 5 Drawing Sheets

(51) Int. Cl.
*A61B 6/00* (2006.01)
*A61B 6/03* (2006.01)

(56) References Cited

U.S. PATENT DOCUMENTS

| | | | |
|---|---|---|---|
| 7,381,959 B2 | 6/2008 | Manjeshwar et al. | |
| 7,626,171 B2 | 12/2009 | Cooke et al. | |
| 7,718,954 B2 | 5/2010 | Wang et al. | |
| 2005/0123183 A1* | 6/2005 | Schleyer et al. | 382/131 |
| 2006/0102845 A1 | 5/2006 | Williams et al. | |
| 2009/0296998 A1* | 12/2009 | Fox et al. | 382/128 |
| 2012/0278055 A1* | 11/2012 | Schweizer et al. | 703/11 |
| 2012/0308106 A1* | 12/2012 | Kelly et al. | 382/131 |
| 2013/0024126 A1* | 1/2013 | Weibrecht | 702/19 |
| 2013/0136328 A1* | 5/2013 | Jansen et al. | 382/131 |
| 2013/0261440 A1* | 10/2013 | Georgi et al. | 600/427 |
| 2014/0119627 A1* | 5/2014 | Skretting et al. | 382/131 |

OTHER PUBLICATIONS

McElroy, D. P., et al.; Singles list mode data processing for MADPET II; 2004; IEEE Nuclear Science Symposium Record; vol. 5; pp. 3325-3329.

* cited by examiner

PET CALIBRATIONS WITH VARYING COINCIDENCE WINDOWS

CROSS REFERENCE TO RELATED APPLICATIONS

This application is a national filing of PCT application Serial No. PCT/IB2011/055097, filed Nov. 15, 2011, published as WO 2012/069960 A2 on May 31, 2012, which claims the benefit of U.S. provisional application Ser. No. 61/416,323 filed Nov. 23, 2010, which is incorporated herein by reference.

The present application finds particular application in positron emission tomography (PET) systems, particularly involving PET scanner calibration. However, it will be appreciated that the described technique may also find application in other medical imaging device calibration systems, other calibration scenarios, or other scanner calibration techniques.

Typical PET scanners perform a normalization calibration to correct non-uniform 3D detector response, as is described in U.S. Pat. No. 7,718,954, which typically requires about 6 hours. Furthermore, such scanners employ a Standard Uptake Value (SUV) calibration that provides the conversion of the counts in an image to an activity concentration. This calibration uses a decaying F-18 source and can take 11-hours or more to complete.

Any event, even two random single events, which are measured by a PET scanner and occur within the coincidence timing window (e.g., 6 ns) and are treated as a coincident event, i.e. as defining a valid line of response (LOR). Reducing the frequency with which random events are taken as valid is beneficial for several reasons. For instance, random event reduction increases the system's maximum NECR (NEMA NU-2 standard, Noise Equivalent Count Rate) performance, and reduces an amount of data for reconstruction processing (speeds up list-mode reconstructions). Additionally, reducing random events reduces the magnitude of the corrections that need to be made during reconstruction, and provides more bandwidth for a PET scanner to acquire valid coincidence events.

Attempts have been made to reduce random events by reducing the coincidence timing window to the minimum required to cover the object being imaged (see, e.g., U.S. Pat. No. 7,626,171). However, in such approaches, a reduced coincidence window changes the counting characteristics of the system, and therefore a separate SUV calibration is required for each coincidence window setting used.

Today, commercial PET scanners have a fixed coincidence window, e.g., about 6 nanoseconds. However, the coincidence window can be shortened with some patients, particularly smaller patients, and/or when performing brain imaging, and the like, to give better discrimination between true events and noise (random events). However, the duration of the coincidence window effects various calibrations including normalization and SUV. Each calibration routine is very time-consumptive, typically taking 11-14 hours or more for each coincidence window.

The present application provides new and improved PET scanner calibration systems and methods that employ interlaced coincidence timing window settings during SUV acquisition on a radioactive calibration phantom, which overcome the above-referenced problems and others.

In accordance with one aspect, a system for that facilitates calibrating a positron emission tomography (PET) scanner includes a PET scanner in which a radioactive calibration phantom is placed and scanned for a predetermined time period, and a processor that executes computer-executable instructions stored in a memory, the instructions including receiving settings for a plurality of selected coincidence timing and/or energy windows. The instructions further include scanning the radioactive calibration phantom and acquiring coincidence data for each of the plurality of coincidence timing and/or energy windows defined by the timing and/or energy window settings during each of a plurality of frames of the predetermined time period. Additionally, the instructions include calculating standard uptake values from a number of photon counts detected in each frame over the predetermined time period for each selected coincidence timing and/or energy window.

In accordance with another aspect, a method of calibrating a positron emission tomography (PET) scanner includes receiving settings a plurality of selected coincidence timing and/or energy windows, and scanning the radioactive calibration phantom and acquiring coincidence data for each of the plurality of coincidence timing and/or energy windows defined by the timing and/or energy window settings during each of a plurality of frames of the predetermined time period. The method further includes calculating standard uptake values (SUVs) from a number of photon counts detected in each frame over the predetermined time period for each selected coincidence timing and/or energy window.

In accordance with another aspect, a PET scanner includes a gantry with a plurality of radiation detectors that detect scintillation events, a coincidence windowing circuit that identifies pairs of detected events within a plurality of coincidence windows of different lengths, and a user input device by which a user selects at least one of the coincidence windows. The PET scanner additionally includes a normalization correction module that applies stored normalization correction values to acquired scan data in the selected coincidence window, an SUV correction module that applies stored SUV correction values to the acquired scan data in the selected coincidence window, and a reconstruction processor that reconstructs the corrected scan data into an image for presentation on a display.

One advantage is that scanner calibration time is reduced.

Another advantage resides in calibrating the scanner for multiple timing windows.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

The subject innovation overcomes the problem of time-consuming and labor-intensive scanner calibrations by reducing the calibration duration by interlacing the coincidence window settings within the SUV calibration. In another embodiment, calibration duration is reduced by performing the SUV and normalization calibration acquisitions at the largest coincidence window and post-processing the data for the desired coincidence windows.

Figure 1:
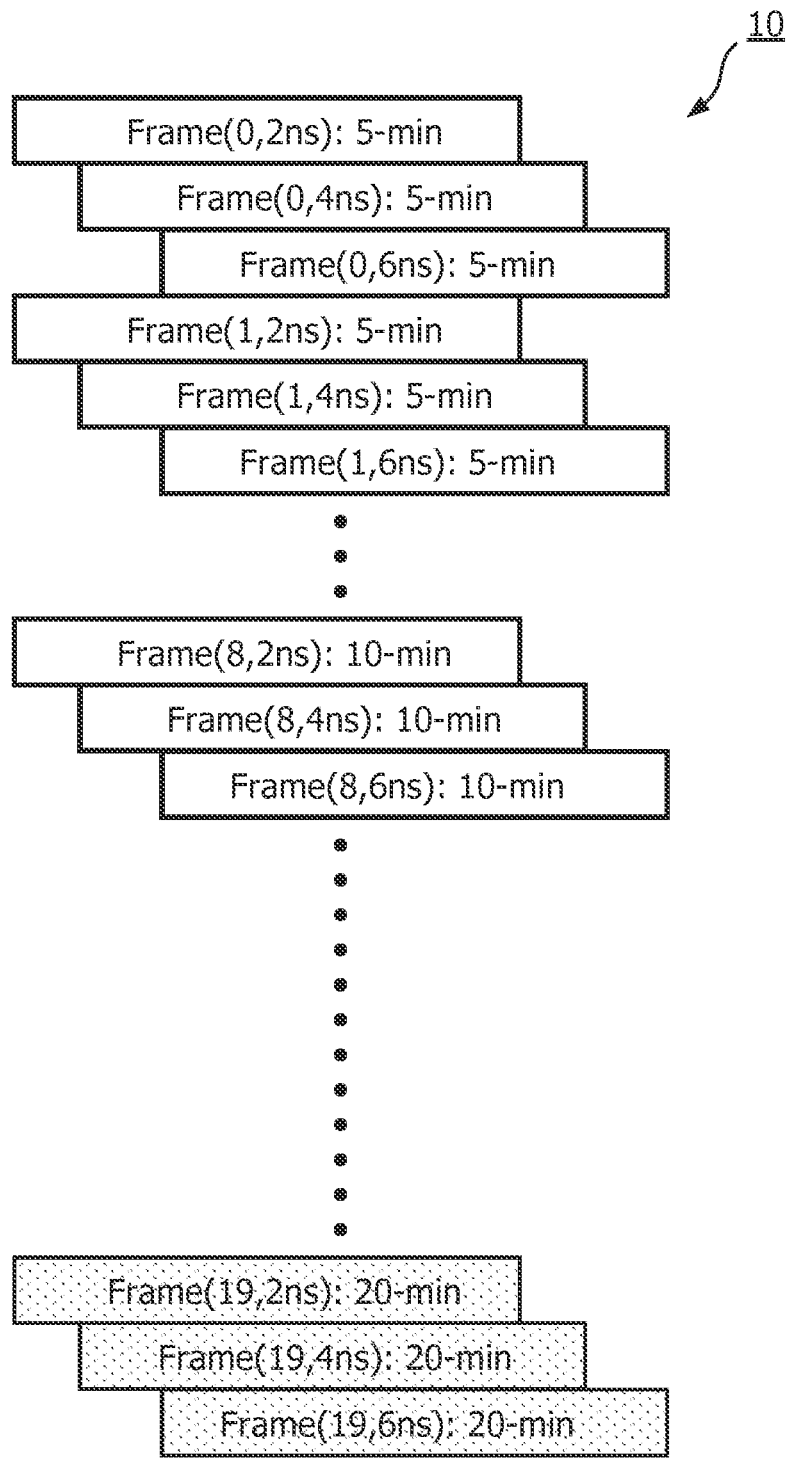
FIG. 1 illustrates a standard uptake value (SUV) acquisition sequence that uses interlaced coincidence window settings to perform a single SUV calibration and normalization for multiple coincidence windows, which eliminates the need for performing separate SUV and normalization calibrations for each coincidence window setting.

FIG. 1 illustrates a standard uptake value (SUV) acquisition sequence 10 that uses interlaced coincidence window settings to perform a single SUV calibration and normalization for multiple coincidence windows, which eliminates the need for performing separate SUV and normalization calibrations for each coincidence window setting. In FIG. 1, three interlaced timing windows (e.g. 2 ns, 4 ns, and 6 ns) are shown for 20 frames (labeled 0-19). Each frame is divided into three portions, each of which corresponds to one of the timing windows. In this manner random events are reduced in a PET scanner the PET scanner's maximum noise equivalent count rate (NECR) is maximized as a function of the diameter of an object being imaged. SUVs are calculated either pixel-wise or over a region of interest (ROI) for each image or frame of a dynamic series at various time points as a ratio of tissue radioactivity concentration. As used herein, a "random event" or "random" denotes an occurrence in which two single events are measured or detected by a PET scanner within a coincidence timing window (e.g., 6 ns or some other predefined timing window), and are mistakenly treated or processed as a coincident event (i.e., as occurring as a result of a single common annihilation event).

As is known in the art, when an electron and positron meet, they annihilate, emitting two 511 keV gamma rays that are oppositely directed in accordance with the principle of conservation of momentum. In PET data acquisition, two substantially simultaneous or coincident 511 keV gamma ray detection events are presumed to have originated from the same positron-electron annihilation event, which is therefore located somewhere along the "line of response" (LOR) connecting the two substantially simultaneous 511 keV gamma ray detection events. This line of response is also sometimes called a projection, and the collected PET data is referred to as projection data.

In conventional PET, two 511 keV gamma ray detection events occurring within a selected short time or coincidence window, such as within 6 nanoseconds of each other, are taken as defining a valid LOR. Due to the variable annihilation position with respect to the detector elements a small (e.g., sub-nanosecond) time difference between the coincident gamma photon detection events occurs. A related technique, called time-of-flight PET or TOF-PET, takes advantage of this small time difference to further localize the positron-electron annihilation event along the LOR. In general, the annihilation event occurred along the LOR at a point closer to the gamma ray detection event that occurred first. If the two gamma ray detection events occur simultaneously within the time resolution of the detectors, then the annihilation event occurred at the midpoint of the LOR.

Under a conventional approach that does not use interlaced collection of calibration data from an F18 phantom, an SUV acquisition sequence for 20 frames (e.g., frames 0-19) takes 11 hours per coincidence window setting. According to an example, SUV data for frames 0-7 takes 15 minutes per frame, for a total of two hours; SUV data acquisition for frames 8-13 takes 30 minutes per frame, for a total of three hours, and SUV data acquisition for frames 14-19 takes one hour per frame, for a total of six hours. One reason that the calibration scan takes so long is that the half life of F18 radioactive material is approximately 110 minutes, so an 11 hour scan provides data over 6 half lives of the material (i.e., after 11 hours, 98.5% of the F18 radioactive material has decayed). Thus, data is needed over an 11 hour period to calibrate photomultipliers in the scanner to a range of radioactivity levels. That is, calibrating the scanner using only data acquired during the first 110 minutes typically does not provide sufficient accuracy for detection of low-level radio activity, such as may be equivalent to calibration data acquired during the $10^{th}$ or $11^{th}$ hour of the calibration scan. Moreover, if a user runs an SUV acquisition sequence for three coincidence window settings (e.g., 2 ns, 4 ns, and 6 ns), then the conventional approach will take 33 hours (using the above F18 example), plus the time to prepare a new F18 calibration phantom for each coincidence window.

The present application has recognized that the calibration only needs to be adequately sampled in each frame, rather than continuously sampled over each entire frame. By interlacing the calibration data collection for a plurality of coincidence windows as shown in FIG. 1, the foregoing example SUV calibration data acquisition sequence can be performed for all three (or more) coincidence window settings in the single 11-hour scanning period with an F18 phantom. FIG. 1 thus provides an example of an approach to modifying the typical SUV calibration acquisition sequence such that the calibration data acquisition for each of the coincidence windows is interlaced within each frame. 2 ns, 4 ns, and 6 ns coincidence window settings are provided in the example of FIG. 1, although other window settings may be employed, as will be appreciated by those of skill in the art. Additionally, more or fewer interlaced window settings (e.g., 2, 3, 4, 5, 6, etc.) may be employed, as will be appreciated by those of skill in the art.

For each frame, data is acquired for all three coincidence windows. For example, rather than spending 15 minutes acquiring data for a single timing window during frame 0, 5 minutes are spent acquiring data for each of three coincidence windows during frame 0. This results in acquisition of only ⅓ of the data for a given coincidence window over all frames when compared to conventional protocols, but the acquired data for each coincidence window is still spread over the entire decay period (e.g., 11-14 hours), which provides more than ample data for SUV characterization and calibration of PMTs in a PET scanner. In this manner, calibration data (SUVs) is acquired for all three (or other number) coincidence windows over the total 11 hour period, which is advantageous because calibration of the scanner for each coincidence window is improved by using data collected over the full radioactive decay period (e.g., 6-7 half lives), but calibration does not require a full 11 hours worth of data for each coincidence window. Rather, periodic samples may be taken for each coincidence window, during each frame taken over the 11 hour period.

In one embodiment, acquisition hardware time stamps each radiation event. The radiation events are subject to the largest coincidence window such that events outside the largest coincidence window to be calibrated can be discarded. Software looks at the time stamps and sorts the coincident pairs by coincidence time, e.g. among events that are coincident within 2 ns, with 4 rs, and within 6 ns. This approach allows the normalization and SUV acquisitions to be run once with the widest coincidence window (e.g., 6 ns) and to generate solutions for other coincidence windows by post-processing.

In one technique, sequential acquisitions at different coincidence windows are used. In one embodiment, calibration frames are processed in real-time (e.g., using hardware, software, or a combination thereof) to simultaneously apply a plurality of coincidence window settings. In another embodiment, calibrations are interlaced to include variation in additional acquisition parameters, e.g. energy window or transverse fields-of-view.

Figure 2:
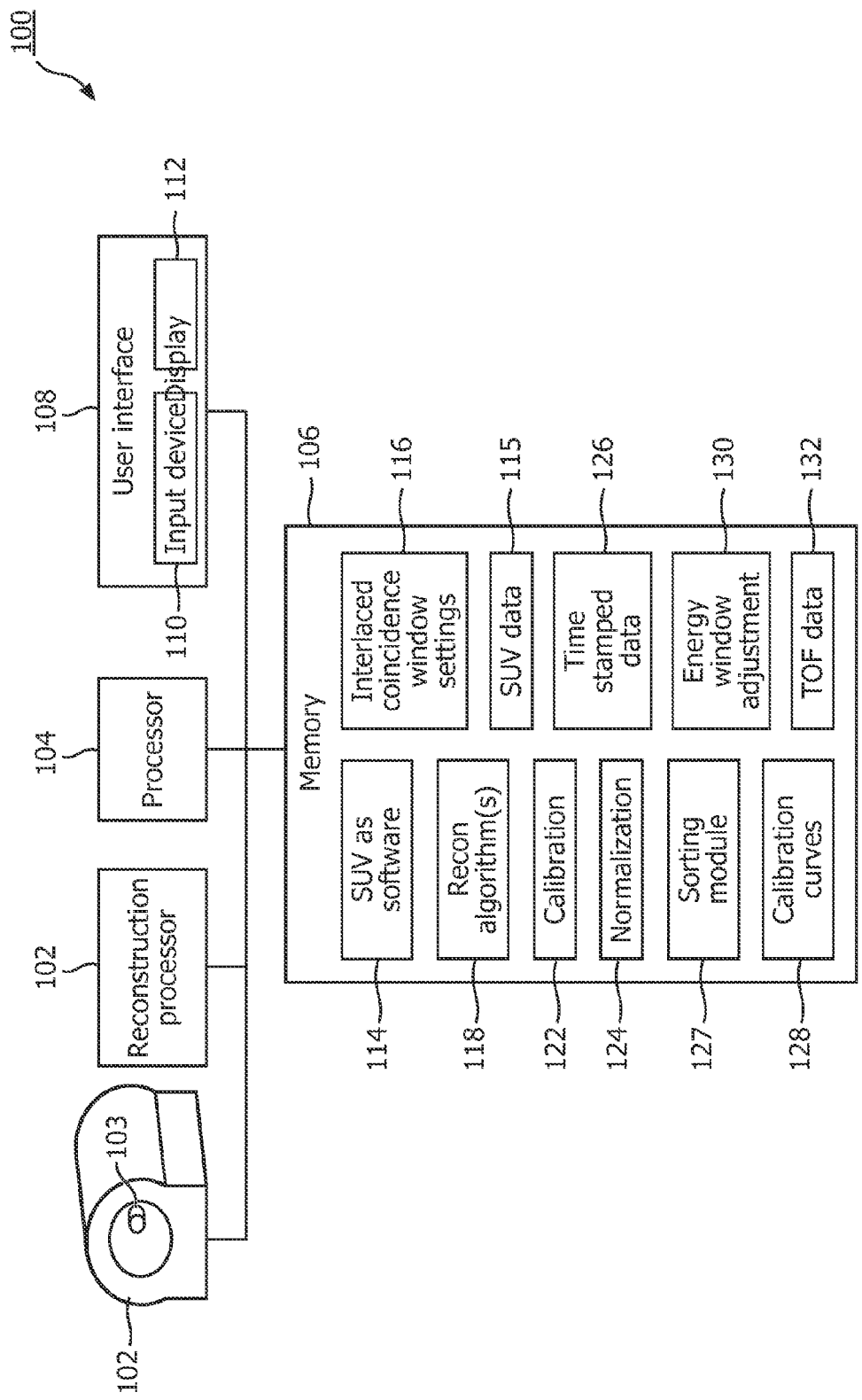
FIG. 2 illustrates a system that facilitates calibrating a PET scanner using interlaced coincidence timing window settings during an SUV acquisition sequence, in accordance with various aspects described herein.

FIG. 2 illustrates a system 100 that facilitates calibrating a PET scanner 102 using a phantom 103, e.g. an F18 phantom. The system 100 includes a processor 104 that is coupled to the PET scanner and to a memory 106. The memory stores, and the processor executes, computer-executable instructions for performing the various functions, methods, techniques, procedures, etc., described herein. The system further includes a user interface 108 comprising one or more input devices 110 (e.g., a keyboard, mouse, stylus, touch screen, microphone, etc.), and a display 112 on which information is presented to a user.

The memory stores an SUV calibration data acquisition sequence software module 114 that is executed by the processor 104 to determine SUV calibration data 115 during a scan of a fludeoxyglucose-18 (F-18) calibration phantom as it radioactively decays in the examination region of the PET scanner (e.g., over an hours-long decay period). The SUV data is used to calculate standard uptake values as a function of coincidence window during the acquisition scan. In one embodiment, the phantom is a 20 cm by 30 cm cylindrical phantom. In another embodiment, the phantom is spherical.

Coincidence window setting information 116 is entered by a user into the user interface 108 and stored in the memory 106. Additionally, the memory stores one or more reconstruction algorithms 118 that are executed by a reconstruction processor 120 in order to reconstruct an image of the calibration phantom and/or other objects after calibration of the PET scanner 102. Once the SUV calibration data 115 has been acquired, the processor executes a calibration module 122 that calibrates standard uptake values for the PET scanner 102. Additionally, the processor executes a normalization module 124 that is stored in the memory to calculate normalize connections for each of the photodetectors or photomultiplier tubes in the PET scanner such that all radiation sensors have a common sensitivity to incident radiation. The normalization calibration is also performed for each coincidence window. The same techniques described above for the SUV calibration can be used to calibrate the normalization for each of the coincidence windows.

The interlaced calibration data collection for each coincidence window facilitates providing an adjustable and/or selectable coincidence window, e.g., of 2, 4, or 6 nanoseconds. SUV and normalization values are calibrated in a single calibration procedure, via the calibration module 122 and the normalization module 124. To perform the SUV calibration, data is typically taken with an F-18 phantom as the F-18 decays over a number of hours, e.g., 14 hours. In one embodiment, data is cyclically collected for each of the coincidence window times to generate a series of points over the 14 hours to define three uptake curves, as shown in the acquisition sequence of FIG. 1.

In another embodiment, all of the data is time-stamped with sufficient accuracy, and the time stamped data 126 is sorted by a sorting module 127 executed by the processor 104 into events which are coincident within 2 nanoseconds, within 4 nanoseconds, or within 6 nanoseconds. These readings and their collection times can be used to generate the SUV calibration curves 128 for each coincidence window.

In another embodiment, an energy window adjustment module 130 provides an adjustable energy window. That is, for acquired F-18 scan data, a width of an energy peak or range of energy around 511 keV that is considered valid is adjustable. However, changing the energy window also changes the SUV and normalization calibrations. In this case, the herein-described techniques are used to calibrate the SUV and the normalization for each of a plurality of energy windows in a single calibration procedure using either the interleaving technique or by recording the energy of each event and sorting by energy window.

According to another embodiment, the nuclear scanner 102 is a time-of-flight (TOF) PET scanner, and TOF data 132 is stored in the memory 106 for use in improving accuracy in the reconstruction of PET images.

As stated above, the system 100 includes the processor 104 that executes, and the memory 106, which stores, computer-executable instructions (e.g., routines, programs, algorithms, software code, etc.) for performing the various functions, methods, procedures, etc., described herein. Additionally, "module," as used herein, denotes a set of computer-executable instructions, software code, program, routine, or the like, as will be understood by those of skill in the art.

The memory may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor can read and execute. In this context, the systems described herein may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

Figure 3:
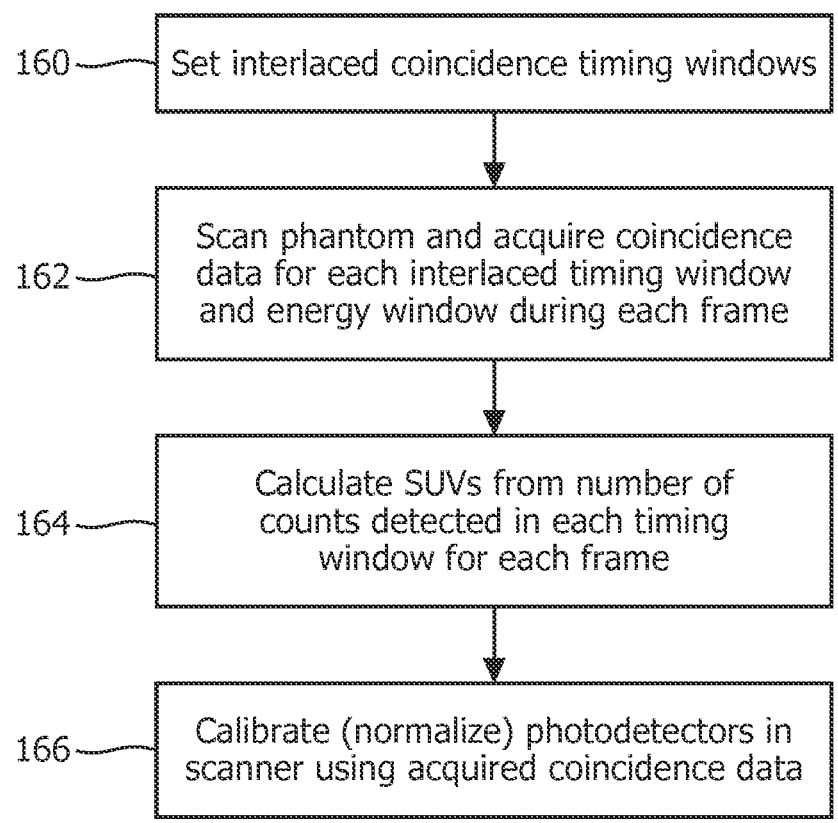
FIG. 3 illustrates a method for calibrating a PET scanner using interlaced coincidence timing windows, in accordance with various aspects described herein.
Figure 4:
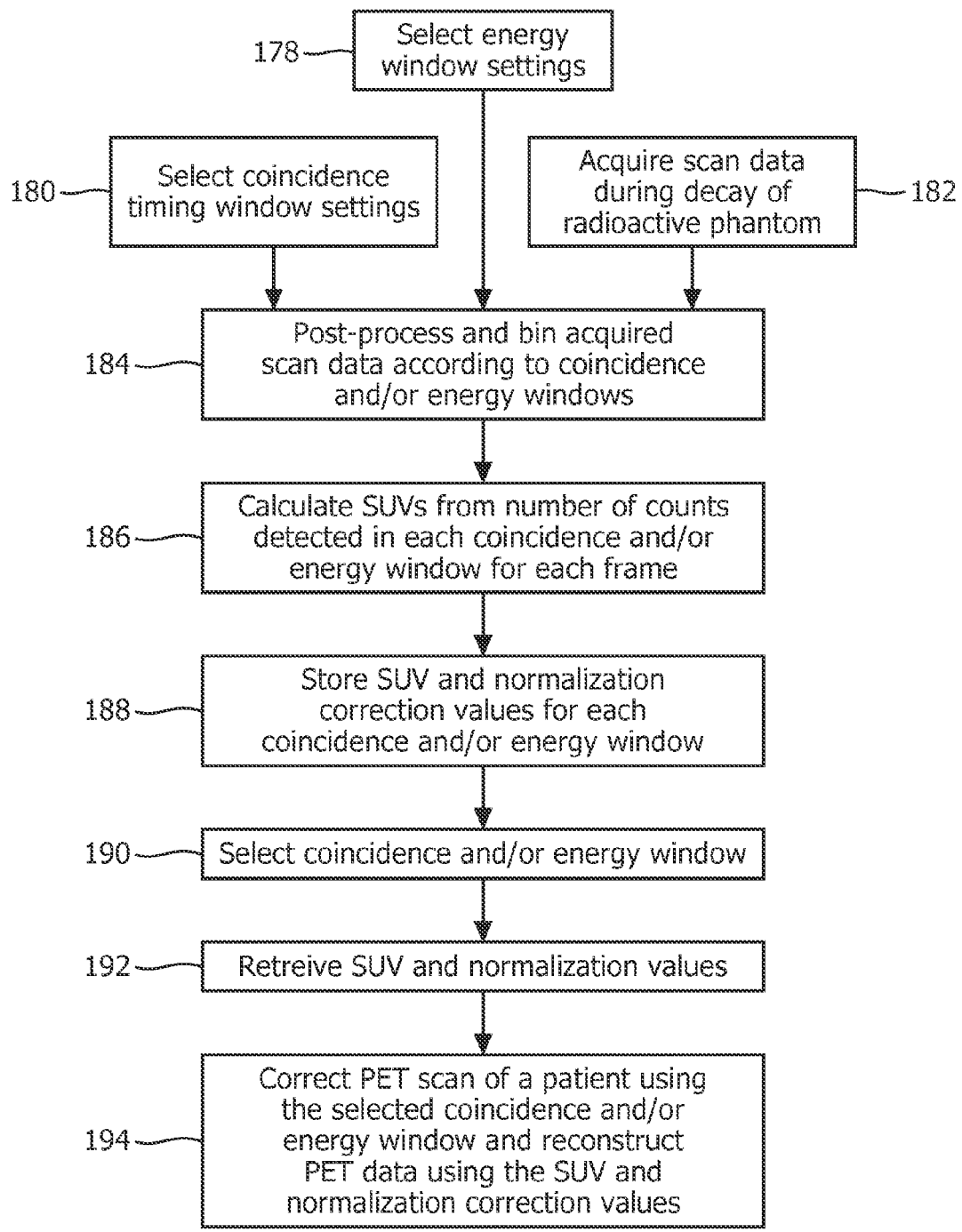
FIG. 4 illustrates a method for calibrating a PET scanner by post-processing acquired coincidence data from a radioactive phantom using interlaced coincidence timing windows to bin the acquired data, in accordance with various aspects described herein.

FIGS. 3 and 4 illustrate a methods related to calibrating PET scanner using interlaced coincidence window settings, in accordance with various features. While the methods herein are described as a series of acts, it will be understood that not all acts may be required to achieve the described goals and/or outcomes, and that some acts may, in accordance with certain aspects, be performed in an order different that the specific orders described.

FIG. 3 illustrates a method for calibrating a PET scanner using interlaced coincidence windows, in accordance with various aspects described herein. At 160, interlaced coincidence windows are selected or set. In one example, three timing windows are set, at 2 ns, 4 ns, and 6 ns, respectively. It will be appreciated however, that other timing window settings (e.g., 1 ns, 1.5 ns, 2.7 ns, 3 ns, 5 ns, etc.) may be set, as well as other numbers of timing windows (e.g., 2, 4, 5, etc.). At 162, a radioactive phantom is scanned and coincidence data is acquired for each of the coincident window settings and each of the energy windows. At 164, coincidence data is analyzed to determine standardized uptake values (SUV) for the phantom in each frame, and for each timing window. The SUV is calculated either pixel-wise or over a region of interest (ROI) for each image or frame of a dynamic series at various time points as a ratio of tissue radioactivity concentration. At 166, photodetectors in the PET scanner are normalized using the acquired coincidence data for each coincidence window setting and each energy window setting. Photodetector calibration typically includes adjusting the spatial gain and offset of an array of photodetectors to ensure spatial and energy consistency and accuracy.

FIG. 4 illustrates a method for calibrating a PET scanner by post-processing acquired coincidence data from a radioactive phantom collect in a list mode. At 178, energy window settings are selected. Detected radiation events that fall outside of the selected energy window(s) will be discarded when correcting acquired scan data for reconstruction. At 180, coincidence timing window settings are selected. Pairs of detected radiation events that fall within the selected coincidence window(s) are used to determine SUVs for scanner calibration and normalization. At 182, a radioactive phantom is scanned to acquire data as the radioactive material decays (e.g., over a 14-hour period or the like). The data is collected in a list mode in which each event is time stamped and its energy recorded. At 184, the list mode data is post-processed to bin or sort the data according to which of a plurality of selected coincidence windows into which particular data falls and/or into which of a plurality of selected energy windows the particle data falls. At 186, coincidence data in each bin is analyzed to calculate standardized uptake values (SUVs) for the phantom in each frame, and for each timing and/or energy window. The SUV is calculated either pixel-wise or over a region of interest (ROI) for each image or frame of a dynamic series at various time points as a ratio of tissue radioactivity concentration. At 188, the SUV and normalization connection values are stored. When a patent is to be scanned, one of the coincidence windows and/or energy windows is selected, at 190. The corresponding SUV and normalization correction values are retrieved, at 192. At 194, PET data is acquired (e.g., the patient is scanned) and corrected in accordance with the retrieved SUV and normalization values. The corrected data is reconstructed into an image for display and/or storage.

Figure 5:
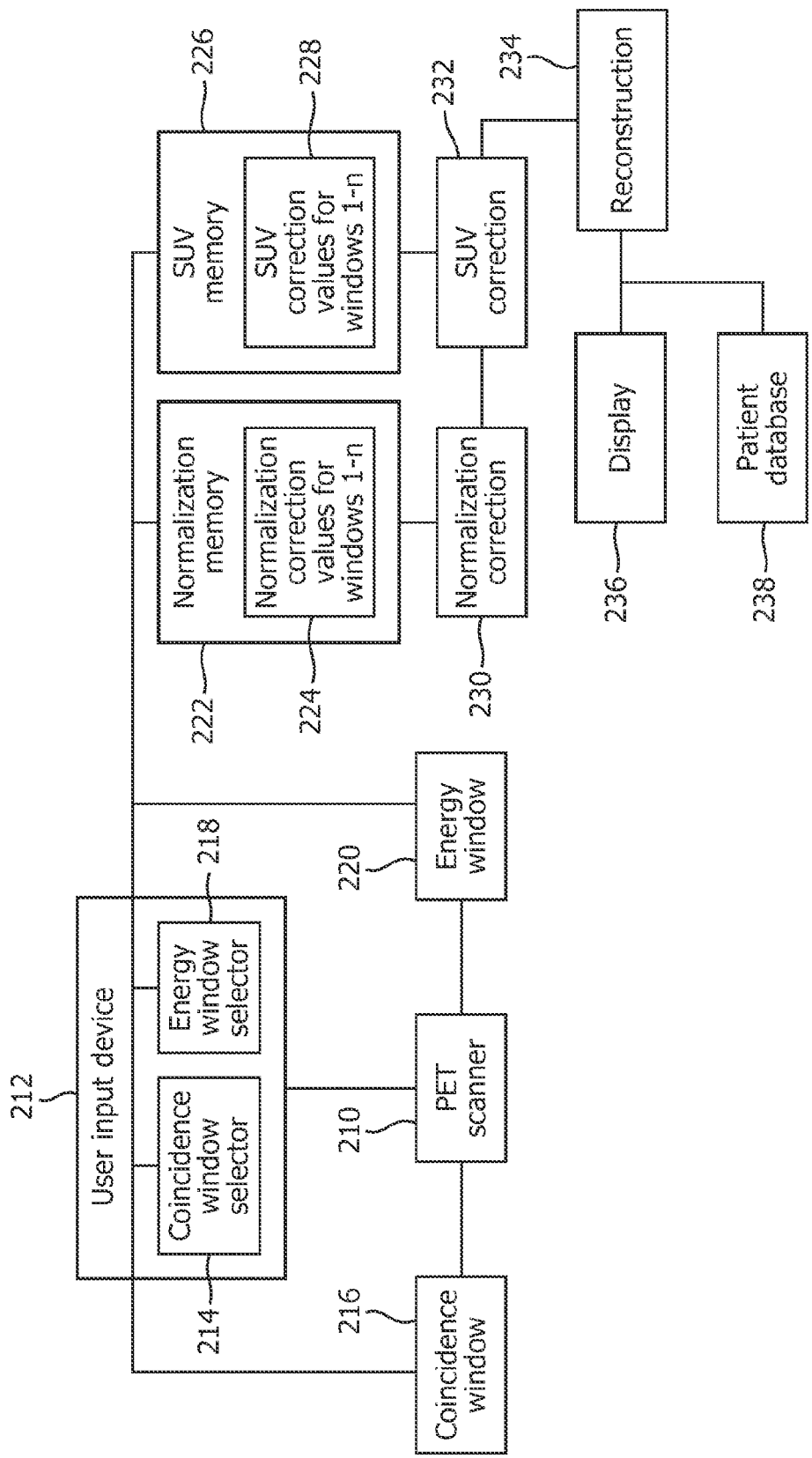
FIG. 5 illustrates a PET scanner calibrated in accordance with one of the above described calibration methods.

FIG. 5 illustrates a PET scanner 210 calibrated in accordance with one of the above described calibration methods. The PET scanner includes a gantry with a plurality of radiation detectors that detect radiation events (e.g., gamma rays, etc.). A user input device 212 is provided, and includes a coincidence window selector 214 via which a user inputs or selects coincidence window settings that delineate one or more coincidence windows into which radiation events are binned or categorized by a coincidence windowing circuit 216. The input device also includes an energy window selector 218 via which a user inputs or selects energy window settings that define one or more energy windows. An energy window circuit 220 excludes or discards detected radiation events that are not within the selected energy window. The coincidence and/or energy windows are used to calibrate the PET scanner as described herein.

The system further includes a normalization memory 222, which stores normalization correction values 224 derived during calibration for a plurality of coincidence timing windows and/or energy windows, and an SUV memory 226 that stores SUV correction values 228 derived during calibration for the plurality of coincidence timing windows and/or energy windows. A normalization correction module (e.g., a processor) retrieves normalization correction values 224 for a given coincidence or energy window used when scanning a subject, and normalizes acquired scan data. An SUV correction module 232 (e.g., a processor) retrieves stored SUV correction values 228 and performs SUV correction on the acquired scan data. A reconstruction processor 234 then reconstructs an image of the subject, which is presented to a user on a display 236, and/or stored in a patient database 238 for later retrieval and display.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A system that facilitates calibrating a positron emission tomography (PET) scanner, including:
 a PET scanner in which a radioactive calibration phantom is placed and scanned for a predetermined time period;
 a processor that executes computer-executable instructions stored in a memory, the instructions including:
  receiving settings for a plurality of selected coincidence timing and/or energy windows;
  scanning the radioactive calibration phantom and acquiring coincidence data for each of the plurality of coincidence timing and/or energy windows defined by the timing and/or energy window settings during each of a plurality of frames of the predetermined time period; and
  calculating standard uptake values from a number of photon counts detected in each frame over the predetermined time period for each selected coincidence timing and/or energy window.

2. The system according to claim 1, the instructions further including generating a calibration curve for each of the timing windows from the standard uptake values, and using the calibration curves to calibrate photodetectors.

3. The system according to claim 1, the instructions further including:
 calculating normalization correction values that correct for differences in sensitivity of the photodetectors in the PET scanner.

4. The system according to claim 1, wherein the radioactive calibration phantom is a fludeoxyglucose-18 (F-18) calibration phantom.

5. The system according to claim 1, wherein the coincidence data is collected in a list mode, and the instructions further include:
 timestamping each received radiation event;
 sorting the radiation events according to which of the plurality of coincidence timing and/or energy windows each pair of coincident events corresponds.

6. The system according to claim 1, wherein the plurality of coincidence timing and/or energy window settings are interlaced and wherein the instructions further include:
 acquiring coincidence data for a plurality of interlaced coincidence timing windows defined by the interlaced coincidence timing and/or energy window settings.

7. The system according to claim 6, wherein the plurality of interlaced coincidence timing windows includes three timing windows having settings of 2 ns, 4 ns, and 6 ns, respectively.

8. The system according to claim 1, the instructions further including:
 storing normalization correction values and SUV correction values for the plurality of coincidence timing windows and/or energy windows;
 performing a PET scan of a subject;
 correcting acquired scan data of the subject using the normalization correction values and the SUV correction values;
 reconstructing an image of the subject using the corrected scan data; and
 storing the reconstructed image to a patient database.

9. The system according to claim 1, wherein the plurality of frames includes approximately 20 frames, acquired over a period of time comprising approximately 6-8 half lives of radioactive material comprised by the radioactive calibration phantom.

10. The system according to claim 1, wherein the PET scanner is a time-of-flight PET scanner.

11. A method of calibrating a positron emission tomography (PET) scanner, including:
receiving settings for a plurality of selected coincidence timing and/or energy windows;
scanning the radioactive calibration phantom and acquiring coincidence data for each of the plurality of coincidence timing and/or energy windows defined by the timing and/or energy window settings during each of a plurality of frames of the predetermined time period; and
calculating standard uptake values (SUVs) from a number of photon counts detected in each frame over the predetermined time period for each selected coincidence timing and/or energy window.

12. The method according to claim 11, further including:
generating a calibration curve for each of the timing windows from the standard uptake values, and using the calibration curves to calibrate photodetectors.

13. The method according to claim 11, further including:
calculating normalization correction values that correct for differences in sensitivity of the photodetectors in the PET scanner.

14. The method according to claim 11, wherein the coincidence data is collected in a list mode, and further including:
timestamping each received radiation event;
sorting the radiation events according to which of the plurality of coincidence timing and/or energy windows each pair of coincident events corresponds.

15. The method according to claim 11, wherein the plurality of coincidence timing and/or energy window settings are interlaced and wherein the instructions further include:
acquiring coincidence data for a plurality of interlaced coincidence timing windows defined by the interlaced coincidence timing and/or energy window settings.

16. The method according to claim 15, wherein the plurality of interlaced coincidence timing windows includes three timing windows having settings of 2 ns, 4 ns, and 6 ns, respectively.

17. The method according to claim 11, further including:
storing normalization correction values and SUV correction values for the plurality of coincidence timing windows and/or energy windows;
performing a PET scan of a subject;
correcting acquired scan data of the subject using the normalization correction values and the SUV correction values;
reconstructing an image of the subject using the corrected scan data; and
storing the reconstructed image to a patient database.

18. The method according to claim 11, wherein the plurality of frames includes approximately 20 frames, acquired over a period of time comprising approximately 6-8 half lives of radioactive material comprised by the radioactive calibration phantom.

19. A processor or computer-readable medium carrying a computer program that controls one or more processors to perform the method of claim 11.

20. A PET scanner, including:
a gantry with a plurality of radiation detectors that detect scintillation events;
a coincidence windowing circuit that identifies pairs of detected events within a plurality of coincidence windows of different lengths;
a user input device by which a user selects at least one of the coincidence windows;
a normalization correction module that applies stored normalization correction values to acquired scan data in the selected coincidence window;
an SUV correction module that applies stored SUV correction values to the acquired scan data in the selected coincidence window; and
a reconstruction processor that reconstructs the corrected scan data into an image for presentation on a display.

21. The system according to claim 20, further including: an energy window circuit that discards detected events that are outside of a user-selected energy window.

22. The system according to claim 20, wherein the plurality of coincidence windows includes coincidence windows of 2 ns, 4 ns, and 6 ns.

* * * * *